United States Patent
Chen et al.

(10) Patent No.: US 6,288,254 B1
(45) Date of Patent: Sep. 11, 2001

(54) BIMETALLIC METALLOCENE CATALYST FOR PREPARING OLEFIN POLYMER

(75) Inventors: Yi-Chun Chen, Hsinchu; Kuang-Kai Liu, Hsinchu Hsien; Jing-Cherng Tsai, Kaohsiung; Bor-Ping Wang, Taoyuan; Hsiao-Fang Li, Chungli; Shu-Hua Chan, Miaoli Hsien, all of (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/334,630

(22) Filed: Jun. 17, 1999

(51) Int. Cl.⁷ .............................. C07F 17/00; C07F 7/00; B01J 31/00
(52) U.S. Cl. ................................. 556/11; 556/12; 556/53; 526/160; 526/943; 502/103; 502/117
(58) Field of Search .................................. 556/11, 12, 53; 502/103, 117; 526/160, 943

(56) References Cited

U.S. PATENT DOCUMENTS

| | | | |
|---|---|---|---|
| 5,372,980 | * 12/1994 | Davis | 502/103 |
| 5,830,958 | * 11/1998 | Peifer et al. | 526/113 |
| 6,010,974 | * 1/2000 | Kim et al. | 502/152 |
| 6,114,556 | * 9/2000 | Aulbach et al. | 556/11 |

* cited by examiner

*Primary Examiner*—Porfirio Nazario-Gonzalez
(74) *Attorney, Agent, or Firm*—Sughrue, Mion, Zinn, Macpeak & Seas, PLLC

(57) ABSTRACT

The present invention provides a novel bimetallic metallocene with a high catalytic activity for preparing olefin polymers having a narrow MWD.

14 Claims, No Drawings

BIMETALLIC METALLOCENE CATALYST FOR PREPARING OLEFIN POLYMER

BACKGROUND OF THE INVENTION

1. Field of the Invention

The present invention relates to a novel bimetallic metallocene, and more particularly to a novel bimetallic metallocene with a high catalytic activity for preparing olefin polymers having a narrow MWD.

2. Description of the Prior Art

Olefin-based polymers have been used in a wide range of applications. One group of commonly used olefin-based polymers is polyolefins, that is, homopolymers or copolymers of olefins. These polyolefin plastics are typically used in such applications as blow and injection molding, extrusion coating, film and sheeting, pipe, wire and cable.

An example of polyolefin is ethylene-propylene elastomer (ethylene-propylene rubbers, EPR). It has many end-use applications due to its resistance to weather, good heat aging properties and its ability to be compounded with large quantities of fillers and plasticizers. Typical automotive uses are radiator and heater hoses, vacuum tubing, weather stripping and sponge doorseals. Typical industrial uses are sponge parts, gaskets and seals.

Another group of commonly used olefin-based polymers is terpolymers of ethylene, propylene, and a non-conjugated diene, which are generally referred to as EPDM elastomers. EPDM elastomers have outstanding weather and acid resistance, and high and low temperature performance properties. Such properties particularly suit EPDM elastomers for use in hoses, gaskets, belts, bumpers, as blending components for plastics and for tire side walls in the automotive industry, and for roofing applications. Additionally, because of their electrical insulation properties, EPDMs are particularly well suited for use as wire and cable insulation.

To date, many catalyst systems have been developed for olefin polymerization, these mainly being classified into two types: Ziegler-Natta catalyst systems and metallocene catalyst systems.

Ziegler et. al. in U.S. Pat. No. 3,113,115 uses $TiCl_4/AlEtCl_2$ catalyst system to produce EPR. Natta et. al. in U.S. Pat. No. 3,300,459 uses $VOCl_3/Al(C_6H_{13})_3$ catalyst system to produce EPR.

Floyd and Hoel in U.S. Pat. Nos. 5,001,205; 4,871,705; and 5,229,478 use metallocenes such as biscyclopentadienyl compounds to produce olefin polymers. The Dow Chemical Company in WO 9,308,221 and European Patent No. 0,416,815 A2 developed monocyclopentadienyl compounds, in which the cyclopentadienyl group is substituted with a constrain-inducing moiety, such as dimethylsilyl. However, synthesis of this particular constrained geometry catalyst (CGC) has a low yield (about 30%).

Davis in U.S. Pat. No. 5,372,980 use a bimetallic metallocene as a catalyst to produce olefin polymers. The catalytic activity is below $1.0 \times 10^5$ g-polymer/g-metal-hr.

SUMMARY OF THE INVENTION

The object of the present invention is to provide a novel bimetallic metallocene with a high catalytic activity for preparing olefin polymers.

Another object of the present invention is to provide a novel bimetallic metallocene capable of producing an olefin polymer having a narrow MWD.

To achieve the above-mentioned object, a novel bimetallic metallocene is developed in the present invention which is represented by the following formula:

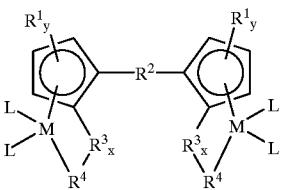

(I)

wherein:

M is zirconium, hafnium, or titanium;

$R^1$ can be the same or different and is independently an alkyl, alkenyl, aryl, alkylaryl or arylakyl group having from 1 to 20 carbon atoms or two adjacent $R^1$ are joined together to form with the carbon atoms to which they are attached a ring system having from 4 to 20 carbon atoms;

$R^2$ is

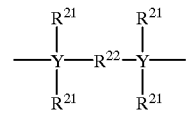

wherein Y can be the same or different and is carbon or silicon or can be deleted, each $R^{21}$ can be the same or different and is hydrogen, an alkyl, aryl, alkylaryl or arylalkyl group having from 1 to 15 carbon atoms or is deleted when Y is deleted, $R^{22}$ is a linear, branched or cyclic alkylene having from 1 to 15 carbon atoms;

$R^3$ is selected from the group consisting of

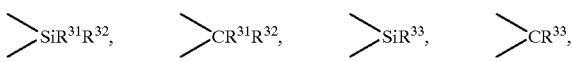

wherein $R^{31}$ and $R^{32}$ can be the same or different and are independently hydrogen, a linear, branched, or cyclic alkyl, aryl, alkylaryl or arylalkyl group having from 1 to 15 carbon atoms, $R^{33}$ is an unsubstituted or substituted alkanediyl group having from 2 to 15 carbon atoms wherein the alkanediyl group forms a ring system with the silicon or carbon atom to which it is attached, the substituent being selected from the group consisting of $C_{1-20}$ alkyl, $C_{1-20}$ alkenyl, $C_{6-20}$ aryl, $C_{7-20}$ alkylaryl, and $C_{7-20}$ arylalkyl;

$R^4$ can be the same or different and is $AR^{41}$, $A(R^{42})_2$, or

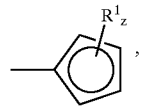

wherein A is nitrogen, phosphorus, or arsenic, $R^{41}$ and $R^{42}$ can be the same or different and is independently hydrogen, a linear, branched or cyclic hydrocarbyl group having from 1 to 20 carbon atoms, $R^1$ is defined as above, and z, which denotes the degree of substitution of the cyclopentadienyl ring, is from 0 to 5;

L is independently an anionic ligand with a −1 valence;
x is 0 or 1;
y, which denotes the degree of substitution of the cyclopentadienyl ring, is from 0 to 4; and
when both $R^4$ are

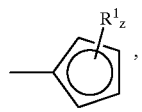

x=1 and at least one $R^3$ is

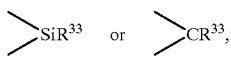

wherein $R^{33}$ is defined as above.

DETAILED DESCRIPTION OF THE INVENTION

The present invention provides a novel metallic metallocene represented by formula (I).

In formula (I), M is a Group IVB transition metal with an oxidation state of +4, such as titanium, zirconium, and hafnium, preferably zirconium.

$R^1$ can be the same or different and is independently an alkyl, alkenyl, aryl, alkylaryl, or arylalkyl group having from 1 to 20 carbon atoms, preferably 1 to 15 carbon atoms. Alternatively, two adjacent $R^1$ groups can be joined together to form with the carbon atoms to which they are attached a ring system having from 4 to 20 carbon atoms, preferably 4 to 6 carbon atoms. Representative examples of $R^1$ include methyl, ethyl, propyl, butyl, isobutyl, amyl, isoamyl, hexyl, 2-ethylhexyl, heptyl, octyl, vinyl, allyl, isopropenyl, phenyl, and tolyl.

Specifically, when two adjacent $R^1$ groups are joined together to form with the carbon atoms to which they are attached a ring system having from 4 to 20 carbon atoms, $R^1$ can form with the cyclopentadienyl moiety on which they are attached a saturated or unsaturated polycyclic cyclopentadienyl ligand such as an indenyl, tetrahydroindenyl, fluorenyl or octahydrofluorenyl group. Representative examples of such ligands include $\eta^5$-cyclopentadienyl, $\eta^5$-methylcyclopentadienyl, $\eta^5$-tetramethylcyclopentadienyl, $\eta^5$-pentamethylcyclopentadienyl, $\eta^5$-n-butylcyclopentadienyl, indenyl, tetrahydroindenyl, fluorenyl, and octahydrofluorenyl.

$R^2$ is

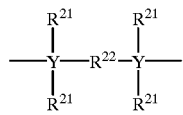

wherein Y can be the same or different and is carbon or silicon or can be deleted. Each $R^{21}$ can be the same or different and is hydrogen, an alkyl, aryl, alkylaryl or arylalkyl group having from 1 to 15 carbon atoms or is deleted when Y is deleted. $R^{22}$ is a linear, branched or cyclic alkylene having from 1 to 15 carbon atoms.

Representative examples of $R^{22}$ groups include ethylene, propylene, butylene, amylene, hexylene, heptylene, octylene, nonylene, decylene, phenylene, biphenylene, terphenylene and the like. Suitable $R^{21}$ groups include methyl, ethyl, propyl, butyl, t-butyl, isobutyl, amyl, isoamyl, hexyl, 2-ethylhexyl, heptyl, octyl, phenyl, tolyl and the like.

$R^3$ is selected from the group consisting of

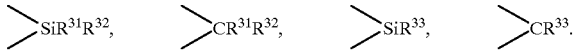

When $R^3$ is

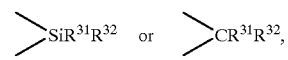

$R^{31}$ and $R^{32}$ can be the same or different and are independently hydrogen, a linear, branched, or cyclic alkyl, aryl, alkylaryl or arylalkyl group having from 1 to 15 carbon atoms. Representative examples of $R^{31}$ and $R^{32}$ include methyl, ethyl, propyl, butyl, t-butyl, isobutyl, amyl, isoamyl, hexyl, 2-ethylhexyl, heptyl, octyl, phenyl, tolyl and the like. Representative examples of $R^{31}$ include dimethylsilanediyl, diethylsilanediyl, and dipropylsilanediyl.

When $R^3$ is

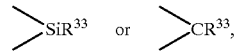

$R^{33}$ is an unsubstituted or substituted alkanediyl group having from 2 to 15 carbon atoms, preferably 3 to 8 carbon atoms, wherein the alkanediyl group forms a ring system with the silicon or carbon atom to which it is attached. The substituent can be $C_{1-20}$ alkyl, $C_{1-20}$ alkenyl, $C_{6-20}$ aryl, $C_{7-20}$ alkylaryl, and $C_{7-20}$ arylalkyl. Representative examples of $R^{33}$ include trimethylene, tetramethylene, pentamethylene, and hexamethylene. Representative examples of $R^3$ include trimethylene silanediyl, tetramethylene silanediyl, pentamethylene silanediyl, and hexamethylene silanediyl.

$R^4$ can be the same or different and is
$AR^{41}$, $A(R^{42})_2$ or

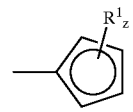

wherein A is nitrogen, phosphorus, or arsenic, $R^{41}$ and $R^{42}$ are the same or different and are independently hydrogen, a linear, branched or cyclic hydrocarbyl group having from 1 to 20 carbon atoms, $R^1$ is defined as above, and z, which denotes the degree of substitution of the cyclopentadienyl ring, is from 0 to 5. $R^{41}$ and $R^{42}$ can be H, $C_{1-20}$ alkyl, $C_{1-20}$ alkenyl, $C_{6-20}$ aryl, $C_{7-20}$ alkylaryl, or $C_{7-20}$ arylalkyl. Suitable $R^{41}$ and $R^{42}$ groups include methyl, ethyl, propyl, butyl, t-butyl, isobutyl, amyl, isoamyl, hexyl, 2-ethylhexyl, heptyl, octyl, phenyl, tolyl and the like.

L is independently an anionic ligand with a −1 valence. Representative examples of L include H, a $C_{1-20}$ hydrocarbon group, a halogen, $C_{6-20}$ aryl, $C_{7-20}$ alkylaryl or arylalkyl, $C_{1-20}$ alkoxy, $C_{1-20}$ oxyaryl, $NH_2$, $NHR^7$, $NR^7R^8$, $-(C=O)NH_2$, $-(C=O)NHR^9$, $-(C=O)NR^9R^{10}$, each of $R^7$, $R^8$, $R^9$ and $R^{10}$ being $C_{1-20}$ alkyl. Suitable L groups include methyl, ethyl, phenyl, chlorine, bromine, methoxy, ethoxy, —NH$_2$, and —N(CH$_3$)$_2$.

In formula (I), x can be 0 or 1, and y, which denotes the degree of substitution of the cyclopentadienyl ring, is from 0 to 4.

When x is 0 ($R^3$ is not present), $R^4$ can be $AR^{42})_2$

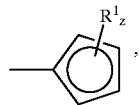

y can be 0 to 4, and z can be 0 to 5.

When x is 1 ($R^3$ is present), $R^4$ can be $AR^{41}$ and

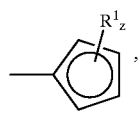

y can be 0 to 3, and z can be 0 to 4.

when both $R^4$ are

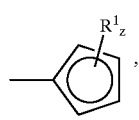

x must be 1 and at least one $R^3$ is

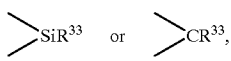

wherein $R^{33}$ is defined as above.

In the present invention, the novel bimetallic metallocene can be combined with an activating coatalyst to form a catalyst composition which can be used for preparing olefin polymers having a narrow MWD, and the catalytic activity is relatively high.

The activating cocatalyst can be an aluminoxane, a trialkyl aluminum, a dialkyl aluminum halide, a salt of an inert and non-coordinating anion, or mixtures thereof.

A commonly used and commercially available aluminoxane is methyl aluminoxane (MAO). The trialkyl aluminum can be selected from the group consisting of trimethyl aluminum, triethyl aluminum, tripropyl aluminum, trisopropyl aluminum, tributyl aluminum, and triisobutyl aluminum (TIBA).

The inert and non-coordinating anion can be a borate. Borates that are suitable for use in the present invention include N,N-dimethyl anilinium tetrakis(pentafluorophenyl) borate, triphenyl carbenium tetrakis(pentafluorophenyl) borate, trimethyl ammonium tetrakis(pentafluorophenyl) borate, ferrocenium tetrakis(pentafluorophenyl)borate, dimethyl ferrocenium tetrakis(pentafluorophenyl)borate, and silver tetrakis(pentafluorophenyl)borate.

Preferably, the activating cocatalyst is methyl aluminoxane, a mixture of triisobutyl aluminum and a borate, or a mixture of triisobutyl aluminum and aluminoxane.

By using the catalyst composition of the present invention (containing the novel bimetallic metallocene and the activating cocatalyst), an olefin polymer can be synthesized. In the presence of a catalytically effective amount of the bimetallic metallocene catalyst of the present invention under polymerizing conditions, an olefin can be subjected to polymerization (i.e., homopolymerization), or an olefin together with another monomer can be subjected to polymerization (i.e., copolymerization).

Suitable olefin monomers can be ethylene or α-olefins. The polymers to be prepared by the process of the present invention can be homopolymers of ethylene, homopolymers of α-olefins, copolymers of α-olefins, and copolymers of ethylene and α-olefins. Examples of the α-olefins include those olefins having 3 to 12 carbon atoms, such as propylene, 1-butene, 1-pentene, 1-hexene, and 1-octene.

More particularly, the catalyst system disclosed in the present invention can be advantageously used to prepare ethylene homopolymers, including high density polyethylene (HDPE) having broad, bimodal, or multimodal, molecular weight distributions for applications such as high molecular weight films and blow molding. Moreover, the bimetallic metallocene catalyst of the present invention is high temperature resistant; therefore, it is very suitable for used in the solution PE system.

Furthermore, the catalyst system disclosed in the present invention can be advantageously used to prepare a copolymer of ethylene and propylene (EPR). Also, a copolymer of ethylene, a $C_{3-12}$ α-olefin, and a non-conjugated diene can be prepared. More particularly, when the $C_{3-12}$ α-olefin used is propylene, a copolymer of ethylene, propylene, and a non-conjugated diene can be prepared, which is referred to as EPDM. The suitable non-conjugated diene can be 5-ethylidene-2-norbornene (ENB), 5-methylene-2-norbornene, 5-vinylidene-2-norbornene, 1,4-hexadiene (HD), or dicyclopentadiene (DCPD).

The novel catalyst system disclosed in the present invention can be used in slurry reaction conditions, gas phase, and solution polymerization reaction conditions. Polymerization is typically carried out at a temperature of 0° to 250° C., and an atmospheric pressure up to 3,000 psi.

The following examples are intended to illustrate the process and the advantages of the present invention more fully without limiting its scope, since numerous modifications and variations will be apparent to those skilled in the art.

SYNTHESIS OF METALLOCENE

Example 1

Preparation of $C_{12}H_{24}[(\eta^5$—$C_9H_5$—$SiMe_2$—$N^tBu)$ Zr $(NMe_2)_2]_2$ 3.1 g (20 mmol) of indenyl potassium salt was placed in a 200 ml schlenk flask and dissolved with 100 ml of toluene. 3.28 g (10 mmol) of 1,12-dibromododecane was added dropwise into the solution at 0° C. under nitrogen. This reaction mixture was allowed to warm up to room temperature and stirred for 5 hours. Then, the reaction solution was stripped by vacuum to dryness, extracted with pentane, stripped again to afford a white solid (3.58 g, yield=90%).

3.58 g (9 mmol) of the white solid was placed in a 200 ml schlenk flask and dissolved with 100 ml of pentane. After the solution was allowed to decreased to 0° C., 11.3 ml of a 1.6 M butyl lithium solution was added dropwise to the solution and stirred for 1 hour at 0° C. The reaction solution was allowed to warm up to room temperature and stirred for 3 hours. The reaction solution was filtered to give (Ind-$C_{12}H_{24}$—Ind)Li$_2$ as a white solid (Yield=95%).

1.55 g (12 mmol) of SiMe$_2$Cl$_2$ was placed in a 100 ml schlenk flask and dissolved with 40 ml of THF. 1.23 g (3 mmol) of (Ind-$C_{12}H_{24}$—Ind)Li$_2$ was added dropwise to the solution under −78° C. The reaction mixture was allowed to warm up to room temperature and stirred overnight. Then, the reaction mixture was stripped to dryness and extracted with pentane to afford a pale yellow liquid (yield=80%).

0.5 g (0.86 mmol) of the above pale yellow liquid and 0.25 g (3.5 mmole) of t-butylamine were dissolved in toluene and stirred under room temperature overnight. The reaction mixture was filtered to remove the amine salt and then stripped to dryness. $C_{12}H_{24}(C_9H_6—SiMe_2—NH^tBu)_2$ was obtained as a orange yellow liquid (Yield=95%).

$C_{12}H_{24}(C_9H_6—SiMe_2—NH^tBu)_2$ (0.55 g, 0.84 mmol) and tetrakis(dimethylamino)zirconium (0.45 g, 1.68 mmol) were dissolved in toluene at 0° C. and then stirred under room temperature overnight. Upon removal of the solvent, $C_{12}H_{24}[(\eta^5—C_9H_5—SiMe_2—N^tBu) Zr (NMe_2)_2]_2$ as a pale yellow product was obtained.

Example 2

Preparation of $C_{12}H_{24}[(\eta^5—C_9H_5—SiC_3H_6—N^tBu) Zr (NMe_2)_2]_2$ 1.69 g (12 mmol) of cyclotrimethylenedichlorosilane was placed in a 100 ml schlenk flask and dissolved with 40 ml of THF (tetrahydrofuran). 1.23 g (3 mmol) of $(Ind-C_{12}H_{24}—Ind)Li_2$ was added dropwise to the solution under −78° C. The reaction mixture was allowed to warm up to room temperature and stirred overnight. Then, the reaction mixture was stripped to dryness and extracted with pentane to afford a pale yellow liquid (yield=78%).

0.6 g (1 mmol) of the above pale yellow liquid and 0.29 g (4 mmole) of t-butylamine were dissolved in toluene and stirred under room temperature overnight. The reaction mixture was filtered to remove the amine salt and then stripped to dryness. $C_{12}H_{24}(C_9H_6—SiC_3H_6—NH^tBu)_2$ was obtained as a orange yellow liquid (Yield=90%).

$C_{12}H_{24}(C_9H_6—SiC_3H_6—NH^tBu)_2$ (0.61 g, 0.9 mmol) and tetrakis(dimethylamino)zirconium (0.48 g, 1.8 mmol) were dissolved in toluene at 0° C. and then stirred under room temperature overnight. Upon removal of the solvent, $C_{12}H_{24}[(\eta^5—C_9H_5—SiC_3H_6—N^tBu)Zr(NMe_2)_2]_2$ as a pale yellow product was obtained.

Example 3

Preparation of $C_5H_{10}[(\eta^5—C_5H_3—SiC_3H_6—\eta^5—C_5H_4) Zr (NMe_2)_2]_2$ 1.1 g (10 mmol) of cyclopentadienyl potassium salt was placed in a 250 ml schlenk flask and dissolved with 70 ml of toluene. 1.62 g (5 mmol) of 1,5-diiodopentane was added dropwise into the solution at 0° C. under nitrogen. This reaction mixture was allowed to warm up to room temperature and stirred for 3 hours. Then, the reaction solution was stripped by vacuum to dryness and extracted with pentane to afford $C_5H_5—C_5H_{10}—C_5H_5$ as a pale yellow liquid (0.72 g, 72% yield).

0.72 g (3.6 mmol) of the pale yellow liquid was placed in a 100 ml schlenk flask and 50 ml of pentane was added. After the mixture solution was allowed to decreased to 0° C., 4.5 ml of a 1.6 M butyl lithium solution was added dropwise to the solution and stirred for 1 hour at 0° C. The reaction solution was allowed to warm up to room temperature and stirred for 3 hours. The reaction solution was filtered to give $(C_5H_4—C_5H_{10}—C_5H_4)Li_2$ as a white solid (Yield=90%).

1.83 g (13 mmol) of cyclotrimethylenedichlorosilane was placed in a 100 ml schlenk flask and dissolved with 40 ml of THF. 0.69 g (3.24 mmol) of $(C_5H_4—C_5H_{10}—C_5H_4)Li_2$ was added dropwise to the solution under −78° C. The reaction mixture was allowed to warm up to room temperature and stirred overnight. Then, the reaction mixture was stripped to dryness and extracted with pentane to afford a pale yellow liquid (1.13 g, 85% yield).

1.13 g of the above pale yellow liquid and 0.4 g (5.5 mmole) of cyclopentadienyl lithium were dissolved in toluene and stirred under room temperature for 5 hours. The reaction mixture was filtered to remove LiCl and then stripped to dryness. $C_5H_{10}(C_5H_4—SiC_3H_6—C_5H_5)_2$ was obtained as a orange yellow liquid (Yield=82%).

$C_5H_{10}(C_5H_4—SiC_3H_6—C_5H_5)_2$ (1.06 g, 2.3 mmol) and tetrakis(dimethylamino)zirconium (1.2 g, 4.5 mmol) were dissolved in toluene at 0° C. and then stirred at room temperature overnight. Upon removal of toluene, $C_5H_{10}[(\eta^5—C_5H_3—SiC_3H_6-\eta^5—C_5H_4)Zr(NMe_2)_2]_2$ as a pale yellow liquid was obtained.

POLYMER SYNTHESIS

Example 4

A 1 liter reactor vessel was purged with nitrogen for 0.5 hours. 500 ml of toluene was charged into the reactor and heated to 120° C. 6.5 ml of MAO (1.49 M) and 3.2 μmol of the catalyst obtained from Example 1 were charged in the reactor and stirred. Ethylene at 150 psi was introduced into the reactor and the reaction proceeded for 0.5 hours. The reaction mixture was filtered and dried to afford 23 g of a final product. The catalytic activity of the catalyst was measured to be $1.58×10^5$ g-PE/g-metal-hr. The polyethylene obtained had a Tm of 133.4° C., a Mw of 215,000, and a MWD of 2.33.

Example 5

A 1 liter reactor vessel was purged with nitrogen for 0.5 hours. 500 ml of toluene was charged into the reactor and heated to 120° C. 30 ml of 1-hexene, 6.5 ml of MAO (1.49 M) and 3. 2 μmol of the catalyst obtained from Example 1 were charged in the reactor and stirred. Ethylene at 150 psi was introduced into the reactor and the reaction proceeded for 0.5 hours. The reaction mixture was filtered and dried to afford 53. 8 g of a final product. The catalytic activity of the catalyst was measured to be 3. $69×10^5$ g-copolymer/g-metal-hr. The copolymer obtained had a Tm of 113.9° C., a Mw of 172,000, and a MWD of 1.88.

Example 6

A 1 liter reactor vessel was purged with nitrogen for 0.5 hours. 500 ml of toluene was charged into the reactor and heated to 120° C. 6.5 ml of MAO (1.49 M) and 3.2 μmol of the catalyst obtained from Example 2 were charged in the reactor and stirred. Ethylene at 150 psi was introduced into the reactor and the reaction proceeded for 0.5 hours. The reaction mixture was filtered and dried to afford 33.6 g of a final product. The catalytic activity of the catalyst was measured to be $2.3×10^5$ g-PE/g-metal-hr.

Example 7

A 1 liter reactor vessel was purged with nitrogen for 0.5 hours. 500 ml of toluene was charged into the reactor and heated to 130° C. 6.4 ml of MAO (1.49 M) and 1.6 μmol of the catalyst obtained from Example 3 were charged in the reactor and stirred. Ethylene at 150 psi was introduced into the reactor and the reaction proceeded for 0.5 hours. The reaction mixture was filtered and dried to afford 57.4 g of a final product. The catalytic activity of the catalyst was measured to be $3.93×10^5$ g-PE/g-metal-hr. The polyethylene obtained had a Tm of 131° C., a Mw of 43,100, and a MWD of 1.85.

Example 8

A 1 liter reactor vessel was purged with nitrogen for 0.5 hours. 500 ml of toluene was charged into the reactor and heated to 130° C. 40 ml of 1-hexene, 6.4 ml of MAO (1.49 M) and 1.6 μg mol of the catalyst obtained from Example 3 were charged in the reactor and stirred. Ethylene at 150 psi was introduced into the reactor and the reaction proceeded for 0.5 hours. The reaction mixture was filtered and dried to afford 69.0 g of a final product. The catalytic activity of the catalyst was measured to be $4.73 \times 10^5$ g-copolymer/g-metal-hr. The copolymer obtained had a Tm of 97° C., a Mw of 23,300, and a MWD of 1.61.

Example 9

A 1 liter reactor vessel was purged with nitrogen for 0.5 hours. 500 ml of toluene was charged into the reactor and heated to 80° C. 40 ml of 1-hexene, 3.2 ml of MAO (1.49 M) and 1.6 μmol of the catalyst obtained from Example 3 were charged in the reactor and stirred. Ethylene at 150 psi was introduced into the reactor and the reaction proceeded for 0.5 hours. The reaction mixture was filtered and dried to afford 18.8 g of a final product. The catalytic activity of the catalyst was measured to be $1.31 \times 10^5$ g-copolymer/g-metal-hr. The copolymer obtained had a Tm of 135° C., a Mw of 71,000, and a MWD of 2.78.

From the above results, it can be seen that the catalyst of the present invention has a high catalytic activity and the polymer obtained by the catalyst of the present invention has a relatively narrow molecular weight distribution.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A bimetallic metallocene which is represented by the following formula:

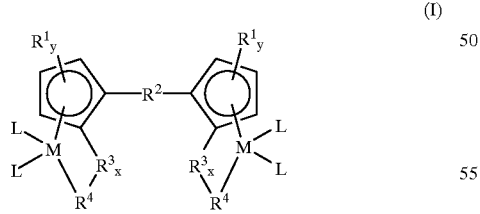

(I)

wherein:

M is zirconium, hafnium, or titanium;

$R^1$ can be the same or different and is independently an alkyl, alkenyl, aryl, alkylaryl or arylalkyl group having from 1 to 20 carbon atoms or two adjacent $R^1$ are joined together to form with the carbon atoms to which they are attached a ring system having from 4 to 20 carbon atoms;

$R^2$ is

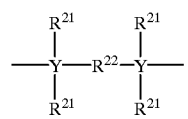

wherein Y can be the same or different and is carbon or silicon or can be deleted, each $R^{21}$ can be the same or different and is hydrogen, an alkyl, aryl, alkylaryl or arylalkyl group having from 1 to 15 carbon atoms or is deleted when Y is deleted, $R^{22}$ is a linear, branched or cyclic alkylene having from 1 to 15 carbon atoms;

$R^3$ is selected from the group consisting of

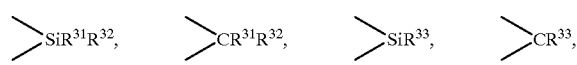

wherein $R^{31}$ and $R^{32}$ can be the same or different and are independently hydrogen, a linear, branched, or cyclic alkyl, aryl, alkylaryl or arylalkyl group having from 1 to 15 carbon atoms, $R^{33}$ is an unsubstituted or substituted alkanediyl group having from 2 to 15 carbon atoms wherein the alkanediyl group forms a ring system with the silicon or carbon atom to which it is attached, the substituent being selected from the group consisting of $C_{1-20}$ alkyl, $C_{1-20}$ alkenyl, $C_{6-20}$ aryl, $C_{7-20}$ alkylaryl, and $C_{7-20}$ arylalkyl;

$R^4$ can be the same or different and is $AR^{41}$, $A(R^{42})_2$, or

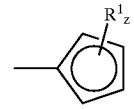

wherein A is nitrogen, phosphorus, or arsenic, $R^{41}$ and $R^{42}$ can be the same or different and is independently hydrogen, a linear, branched or cyclic hydrocarbyl group having from 1 to 20 carbon atoms, $R^1$ is defined as above, and z, which denotes the degree of substitution of the cyclopentadienyl ring, is from 0 to 5;

L is independently an anionic ligand with a −1 valence;

x is 0 or 1;

y, which denotes the degree of substitution of the cyclopentadienyl ring, is from 0 to 4; and

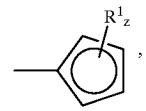

when both $R^4$ are
x=1 and at least one $R^3$ is

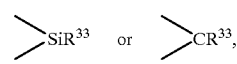

wherein $R^{33}$ is defined as above;

when x=1, $R^4$ is selected from the group consisting of $AR^{41}$, $A(R^{42})_2$, and

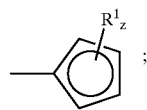

when x=0, at least one $R^4$ is $AR^{41}$.

2. The metallocene as claimed in claim 1, wherein M is zirconium.

3. The metallocene as claimed in claim 1, wherein two adjacent $R^1$ are joined together forming with the cyclopentadienyl moiety on which they are attached a saturated or unsaturated polycyclic cyclopentadienyl ligand.

4. The metallocene as claimed in claim 3, wherein two adjacent $R^1$ are joined together forming with the cyclopentadienyl moiety on which they are attached an indenyl, tetrahydroindenyl, fluorenyl or octahydrofluorenyl group.

5. The metallocene as claimed in claim 1, wherein y is 0.

6. The metallocene as claimed in claim 1, wherein Y is carbon.

7. The metallocene as claimed in claim 6, wherein $R^{22}$ is a linear alkylene having from 1 to 15 carbon atoms.

8. The metallocene as claimed in claim 7, wherein $R^2$ is dodecylene or pentylene.

9. The metallocene as claimed in claim 1, wherein A is nitrogen, $R^{41}$ is tert-butyl.

10. The metallocene as claimed in claim 9, wherein $R^3$ is dimethylsilanediyl.

11. The metallocene as claimed in claim 1, wherein $R^3$ is an alkanediyl silanediyl group from 2 to 8 carbon atoms; wherein the alkanediyl group forms a ring system with the silicon atom to which it is attached.

12. The metallocene as claimed in claim 11, wherein $R^3$ is trimethylene silanediyl.

13. The metallocene as claimed in claim 1, wherein L is selected from the group consisting of H, a $C_{1-20}$ hydrocarbon group, a halogen, $C_{6-20}$ aryl, $C_{7-20}$ arylalkyl or alkylaryl, $C_{1-20}$ alkoxy, $C_{1-20}$ oxyaryl, $NH_2$, $NHR^7$, $NR^7R^8$, —(C=O)$NH_2$, —(C=O)$NHR^9$, —(C=O)$NR^9R^{10}$, each of $R^7$, $R^8$, $R^9$ and $R^{10}$ being $C_{1-20}$ alkyl.

14. The metallocene as claimed in claim 13, wherein L is —$N(CH_3)_2$.

* * * * *